US00PP30238P3

(12) United States Plant Patent
Arts

(10) Patent No.: US PP30,238 P3
(45) Date of Patent: Feb. 26, 2019

(54) ***HYDRANGEA* PLANT NAMED 'H216905'**

(50) Latin Name: *Hydrangea macrophylla*
Varietal Denomination: H216905

(71) Applicant: Niels Arts, Aalsmeer (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 4 days.

(21) Appl. No.: 15/731,674

(22) Filed: Jul. 15, 2017

(65) Prior Publication Data

US 2019/0021199 P1 Jan. 17, 2019

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

(56) References Cited

PUBLICATIONS

UPOV hit on *Hydrangea* plant named, 'H216905', QZ PBR 20163255, filed Dec. 22, 2016.*
EU PBR application, Dec. 22, 2016, *Hydrangea* Breeders Assoc.

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'H216905', characterized by its upright and rounded plant habit; vigorous growth habit and moderate growth rate; freely branching habit with strong, thick and sturdy stems; early, freely and uniformly flowering habit; mophead-type inflorescences with numerous light red purple-colored sterile flowers; sterile flowers with undulating and curled sepals; and good postproduction longevity.

3 Drawing Sheets

Botanical designation: *Hydrangea macrophylla.*
Cultivar denomination: 'H216905'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H216905'.

The new *Hydrangea* plant is a product of a planned breeding program conducted by the Inventor in De Kwakel, The Netherlands. The objective of the breeding program was to create new freely-branching *Hydrangea* plants with strong sturdy stems, large inflorescences with numerous showy sterile flowers, attractive sterile flower color and good postproduction longevity.

The new *Hydrangea* plant originated from a cross-pollination made by the Inventor in April, 2011 in De Kwakel, The Netherlands, of a proprietary selection of *Hydrangea macrophylla* identified as code number 07-0166-002, not patented, as the female, or seed, parent with a proprietary selection of *Hydrangea macrophylla* identified as code number 03-0134-219, not patented, as the male, or pollen, parent. The new *Hydrangea* plant was discovered and selected by the Inventor as a single flowering plant from within the progeny of the stated cross-pollination in a controlled greenhouse environment in De Kwakel, The Netherlands in March, 2013.

Asexual reproduction of the new *Hydrangea* plant by vegetative cuttings in a controlled environment in De Kwakel, The Netherlands since June, 2013 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H216905'. These characteristics in combination distinguish 'H216905' as a new and distinct *Hydrangea* plant:

1. Upright and rounded plant habit.
2. Vigorous growth habit and moderate growth rate.
3. Freely branching habit with strong, thick and sturdy stems.
4. Early, freely and uniformly flowering habit.
5. Mophead-type inflorescences with numerous light red purple-colored sterile flowers.
6. Sterile flowers with undulating and curled sepals.
7. Good postproduction longevity.

Plants of the new *Hydrangea* can be compared to plants of the female and male parent selections. Plants of the new *Hydrangea* differ primarily from plants of the female and male parent selections in sterile flower sepals as plants of the new *Hydrangea* have sterile flower sepals that are undulating and curled whereas sterile flower sepals of plants of the female and male parent selections are mostly flat and not undulating and curled.

Plants of the new *Hydrangea* can be compared to plants of the *Hydrangea hybrida* 'Agrihydravijf', disclosed in U.S. Plant Pat. No. 19,731. In side-by-side comparisons, plants of the new *Hydrangea* differ primarily from plants of 'Agrihydravijf' in the following characteristics:

1. Plants of the new *Hydrangea* have lighter green-colored leaves than plants of 'Agrihydravijf'.
2. Plants of the new *Hydrangea* have shorter panicles than plants of 'Agrihydravijf'.
3. Plants of the new *Hydrangea* have sterile flower sepals that are undulating and curled whereas sterile flower sepals of plants of 'Agrihydravijf' are mostly flat and not undulating and curled.
4. Plants of the new *Hydrangea* have sterile flower sepal margins that are entire whereas sterile flower sepal margins of plants of 'Agrihydravijf' are serrate to dentate.
5. Plants of the new *Hydrangea* have darker red purple-colored sterile flower sepals than plants of 'Agrihydravijf'.
6. When "blued", plants of the new *Hydrangea* have light blue-colored sterile flower sepals whereas plants of 'Agrihydravijf' have light violet blue-colored sterile flowers sepals.
7. Plants of the new *Hydrangea* have more fertile flowers per inflorescence than plants of 'Agrihydravijf'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a top perspective view of a typical flowering plant of 'H216905'.

The photograph on the second sheet is a side perspective view of a typical flowering plant of 'H216905' that has been "blued", that is, treated with aluminum sulfate.

The photograph on the third sheet is a close-up view of a typical inflorescence of 'H216905' that has been "blued".

DETAILED BOTANICAL DESCRIPTION

Plants used in the aforementioned photographs and in the following description were grown during the spring in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were pinched one time and were ten months old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H216905'.

Parentage:

*Female, or seed, parent.*—Proprietary selection of *Hydrangea macrophylla* identified as code number 07-0166-002, not patented.

*Male, or pollen, parent.*—Proprietary selection of *Hydrangea macrophylla* identified as code number 03-0134-219, not patented.

Propagation:

*Type cutting.*—By vegetative cuttings.

*Time to initiate roots, summer.*—About two weeks at temperatures about 23° C.

*Time to initiate roots, winter.*—About 18 days at temperatures about 18° C.

*Time to produce a rooted young plant, summer.*—About four weeks at temperatures about 23° C.

*Time to produce a rooted young plant, winter.*—About five weeks at temperatures about 18° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright and rounded plant habit; strong and sturdy stems; moderate growth rate and vigorous growth habit.

*Plant height.*—About 25 cm to 40 cm.

*Plant diameter or area of spread.*—About 30 cm to 40 cm.

Lateral branch description:

*Branching habit.*—Freely branching habit; when pinched, about six to eight lateral branches develop per plant.

*Length.*—About 25 cm.

*Diameter.*—About 4 mm to 5 mm.

*Internode length.*—About 3 cm to 4 cm.

*Texture.*—Smooth, glabrous; fully developed, woody.

*Aspect.*—Upright to about 20° from vertical.

*Strength.*—Strong, sturdy.

*Color.*—When developing: Close to 144C; at internodes, close to 187B; lenticels, close to 187A. Developed: Close to 144B; at the internodes, close to 187B; when woody, close to 177C; lenticels, close to 187A.

Leaf description:

*Arrangement.*—Opposite, simple.

*Length.*—About 11 cm.

*Width.*—About 6 cm to 8 cm.

*Shape.*—Ovate.

*Apex.*—Acute.

*Base.*—Obtuse.

*Margin.*—Serrulate.

*Texture, upper surface.*—Smooth to rugose, glabrous.

*Texture, lower surface.*—Rugose, glabrous.

*Venation pattern.*—Pinnate.

*Color.*—Developing and fully developed leaves, upper surface: Close to 137C; venation, close to 145B. Developing and fully developed leaves, lower surface: Close to 144B; venation, close to 145C.

*Petioles.*—Length: About 2 cm to 2.5 cm. Diameter: About 3 mm to 4 mm. Texture, upper and lower surfaces: Smooth, glabrous. Color, upper surface: Close to 145B. Color, lower surface: Close to 145C.

Flower description:

*Flower type and habit*.—Showy sterile flowers that are undulating and curled, and small inconspicuous fertile flowers arranged on mophead-type terminal panicles; panicles globular and slightly flattened in shape; flowers face upright to outwardly depending on their position in the inflorescence.

*Fragrance*.—None detected.

*Natural flowering season*.—Early flowering habit, plants begin flowering about 41 to 60 weeks after planting; flowering begins in the early summer and is continuous throughout the summer in Northern Europe.

*Flower longevity*.—Fertile flowers last about one month on the plant, fertile flowers not persistent; sterile flowers last about four months on the plant, sterile flowers persistent.

*Quantity of flowers*.—Freely flowering habit; about 80 to 120 fertile flowers per panicle and about 80 sterile flowers per panicle.

*Panicle height*.—About 8 cm to 10 cm.

*Panicle diameter*.—About 12 cm to 15 cm.

*Fertile flower buds*.—Length: About 3 mm. Diameter: About 3 mm. Shape: Rounded. Color: Close to 144D.

*Sterile flower buds*.—Length: About 3 mm. Diameter: About 3 mm. Shape: Rounded. Color: Close to 144A.

*Fertile flower diameter*.—About 3 mm.

*Fertile flower depth* (*height*).—About 3 mm.

*Sterile flower diameter*.—About 3.5 cm to 4 cm.

*Sterile flower depth* (*height*).—About 1 cm.

*Petals, fertile flowers*.—Quantity and arrangement: Five in a single whorl. Length: About 3 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 149D. Fully opened, upper surface: Close to 75C; color does not change with development. Fully opened, lower surface: Close to 75D; color does not change with development.

*Petals, sterile flowers*.—Quantity and arrangement: About four to five in a single whorl. Length: About 2 mm. Width: About 1.5 mm. Shape: Ovate. Apex: Acute. Base: Cuneate. Margin: Entire. Texture, upper and lower surfaces: Smooth, glabrous. Color: When opening, upper and lower surfaces: Close to 149D; when "blued", close to 145D. Fully opened, upper surface: Close to 75C; when "blued", close to 149D; colors do not change with development. Fully opened, lower surface: Close to 75D; when "blued", close to 149D; colors do not change with development.

*Sepals, fertile flowers*.—Quantity and arrangement: Five in a single whorl. Length: About 2.5 mm. Width: About 1.5 mm. Shape: Ovate. Apex: Acute. Base: Obtuse. Margin: Entire. Texture, upper and lower surfaces: Smooth, glabrous. Color: When opening, upper and lower surfaces: Close to 145C. Fully opened, upper and lower surfaces: Close to 149D; color does not change with development.

*Sepals, sterile flowers*.—Quantity and arrangement: Four to five in a single whorl. Length: About 2 cm to 2.5 cm. Width: About 2 cm to 2.5 cm. Shape: Deltoid, undulating and curled. Apex: Rounded. Base: Obtuse. Margin: Entire. Texture, upper and lower surfaces: Smooth, glabrous. Color: When opening, upper and lower surfaces: Close to 149D; when "blued", close to 145D. Fully opened, upper and lower surfaces: Close to N74D; when "blued", close to 107C; colors do not change with development.

*Pedicels, fertile flowers*.—Length: About 5 mm. Diameter: About 1 mm. Strength: Strong. Aspect: Mostly upright. Texture: Smooth, glabrous. Color: Close to 69C.

*Pedicels, sterile flowers*.—Length: About 2 cm to 2.5 cm. Diameter: About 2 mm to 3 mm. Strength: Strong. Aspect: Erect to about 45° from vertical. Texture: Smooth, glabrous. Color: Close to 73D.

*Reproductive organs, fertile flowers only; sterile flowers without reproductive organs*.—Stamens: Quantity per flower: Eight. Filament length: About 1 mm. Filament color: Close to 155D. Anther length: About 1 mm. Anther shape: Conical. Anther color: Close to 145D. Pollen amount: Abundant. Pollen color: Close to 155D. Pistils: Pistil quantity per flower: Three. Pistil length: About 3 mm. Stigma shape: Oval. Stigma color: Close to 155B. Style length: About 1 mm. Style color: Close to 155B. Ovary color: Close to 155B.

*Seeds*.—Quantity per fertile flower: About 20 to 30. Length: About 0.5 mm. Diameter: About 0.1 mm. Color: Close to 200C.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'H216905' as illustrated and described.

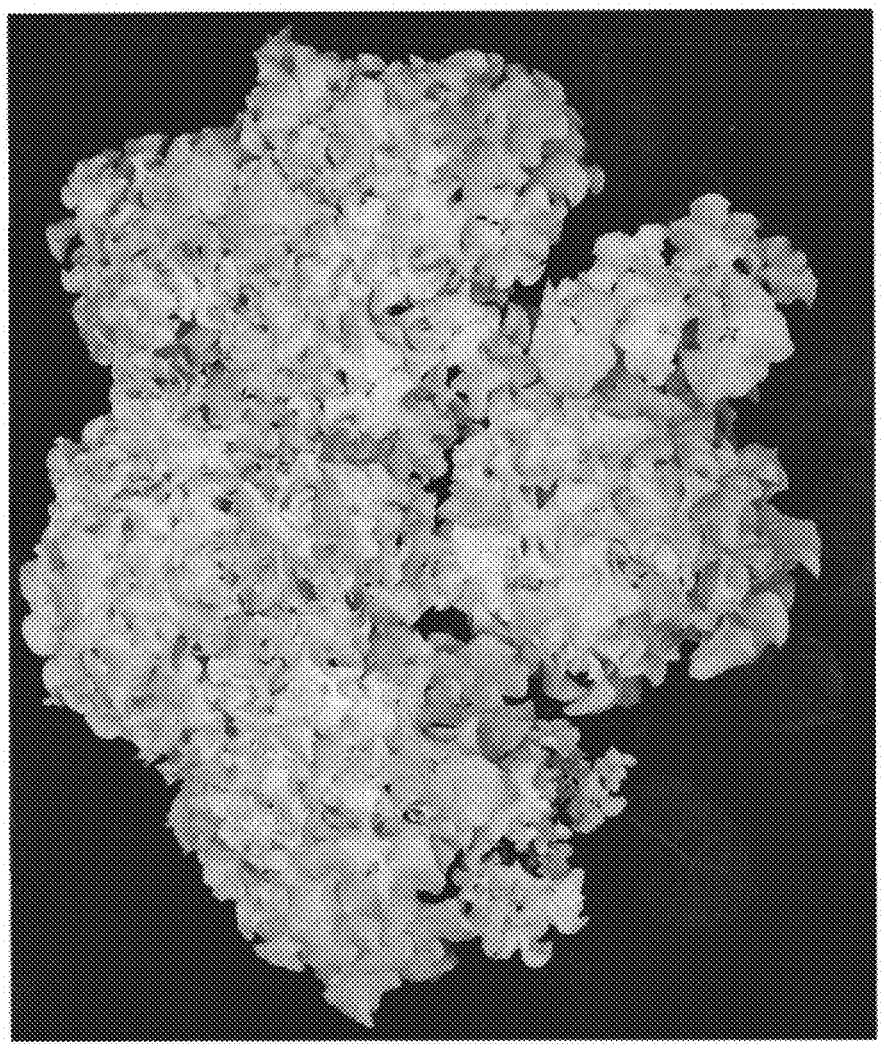

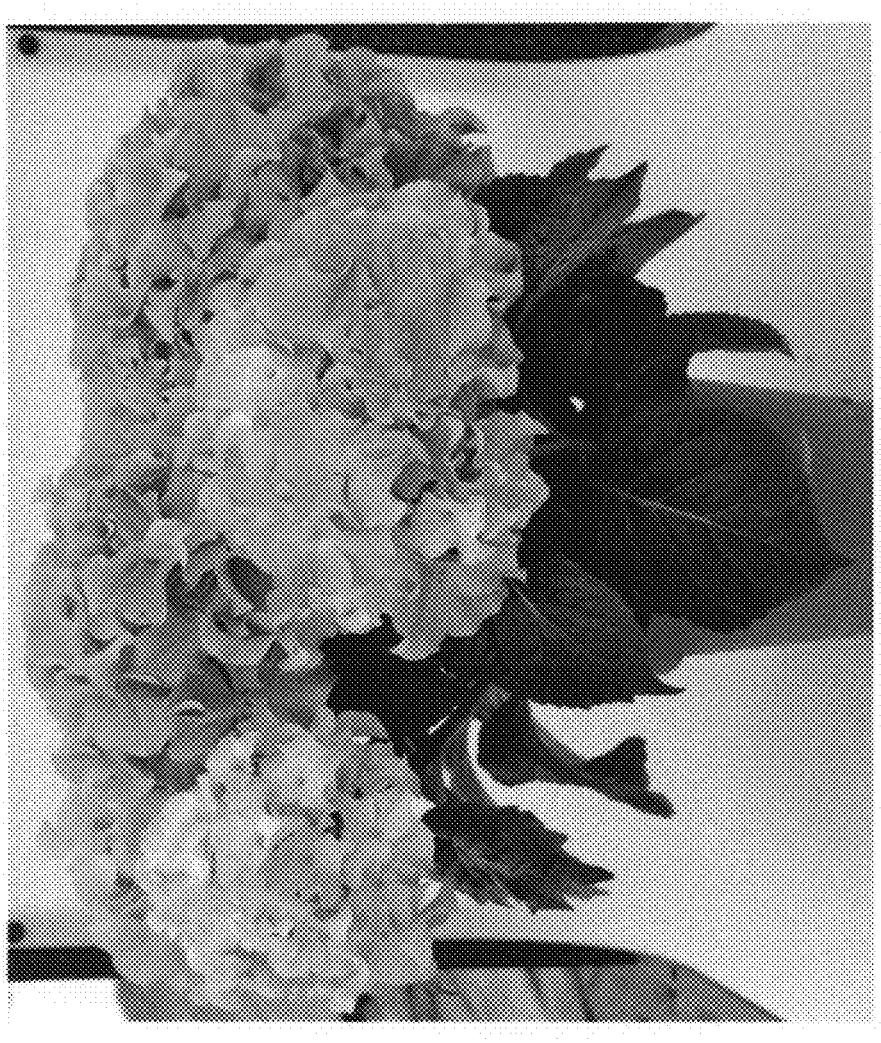

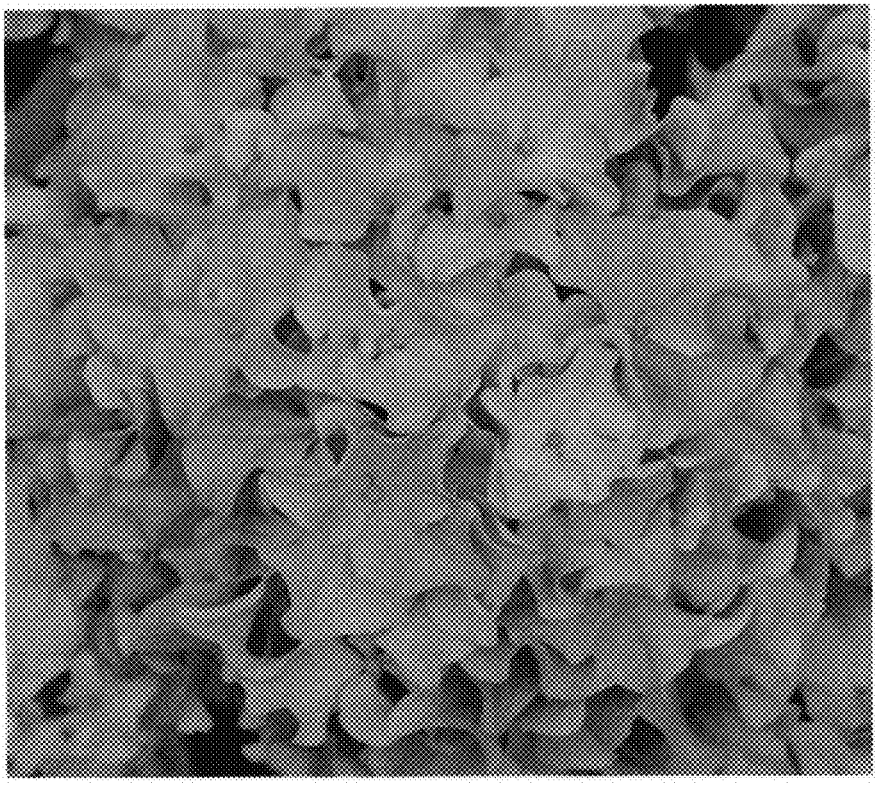

* * * * *